US010591501B2

(12) United States Patent
Matthias et al.

(10) Patent No.: US 10,591,501 B2
(45) Date of Patent: Mar. 17, 2020

(54) AUTOMATIC STRUCTURE DETERMINATION

(71) Applicants: Torsten Matthias, Wendelsheim (DE); Hans-Peter Schimon, Heiningen (DE); Jens Blecken, Fuerfeld (DE); Markus Wulf, Alzey (DE); Matthias Wende, Mommenheim (DE)

(72) Inventors: Torsten Matthias, Wendelsheim (DE); Hans-Peter Schimon, Heiningen (DE); Jens Blecken, Fuerfeld (DE); Markus Wulf, Alzey (DE); Matthias Wende, Mommenheim (DE)

(*) Notice: Subject to any disclaimer, the term of this patent is extended or adjusted under 35 U.S.C. 154(b) by 1678 days.

(21) Appl. No.: 14/355,124

(22) PCT Filed: Oct. 29, 2012

(86) PCT No.: PCT/EP2012/004527
§ 371 (c)(1),
(2) Date: Apr. 29, 2014

(87) PCT Pub. No.: WO2013/064237
PCT Pub. Date: May 10, 2013

(65) Prior Publication Data
US 2019/0195904 A1    Jun. 27, 2019

(30) Foreign Application Priority Data

Oct. 31, 2011   (DE) .................. 10 2011 117 273
Oct. 26, 2012   (EP) ............... PCT/EP2012/004492

(51) Int. Cl.
*G01N 35/00*     (2006.01)
*C12M 1/34*      (2006.01)
(Continued)

(52) U.S. Cl.
CPC ....... *G01N 35/04* (2013.01); *G01N 35/00029* (2013.01); *G01N 35/025* (2013.01);
(Continued)

(58) Field of Classification Search
CPC ............. G01N 33/54306; G01N 35/00; G01N 35/028; G01N 21/0303; G01N 21/645
(Continued)

(56) References Cited

U.S. PATENT DOCUMENTS

2002/0186875 A1* 12/2002 Burmer .............. G06K 9/00127
                                                        382/133

FOREIGN PATENT DOCUMENTS

WO   WO-2011049608 A2 *  4/2011  ........... G02B 21/245

* cited by examiner

*Primary Examiner* — Monzer R Chorbaji
(74) *Attorney, Agent, or Firm* — Buchanan Ingersoll & Rooney PC

(57) ABSTRACT

The invention relates to an automated method for the optical analysis of structures, in particular for the analysis and determination of biological cellular structures, and to an apparatus for this purpose, wherein an electro-optical unit generates an electronic image of two- and three-dimensional structures present in the sample, a storage medium stores the image, a computer-controlled displacement device establishes an optimized image sharpness of the image by changing the distance between sample and the optical unit, wherein the displacement device is controlled by contrast analysis and color value detection, and a computer unit compares the images generated by the electro-optical unit of two- and/or three-dimensional structures with the known structures stored in a database, and the structures registered by the optical unit are assigned by means of an algorithm to characteristic grids, structures or patterns.

12 Claims, 3 Drawing Sheets

(51) Int. Cl.
  *G01N 21/29* (2006.01)
  *G06K 9/00* (2006.01)
  *G06K 9/62* (2006.01)
  *G01N 35/04* (2006.01)
  *G02B 21/36* (2006.01)
  *G01N 35/02* (2006.01)
  *G02B 21/24* (2006.01)
(52) U.S. Cl.
  CPC ......... *G02B 21/241* (2013.01); *G02B 21/245* (2013.01); *G02B 21/365* (2013.01); *G01N 2035/00138* (2013.01); *G01N 2035/0415* (2013.01); *G01N 2035/0441* (2013.01)
(58) Field of Classification Search
  USPC .......... 422/50, 82.05, 561; 436/43; 382/133, 382/157, 224; 435/287.3
  See application file for complete search history.

AUTOMATIC STRUCTURE DETERMINATION

CROSS-REFERENCE TO RELATED APPLICATIONS

This application is a National Stage Application of PCT/EP2012/004527 filed Oct. 29, 2012, which claims priority from German Application No. DE 10 2011 117 273.8 filed on Oct. 31, 2011 and PCT/EP2012/004492 filed Oct. 26, 2012. Each of these applications is hereby incorporated by reference herein in its entirety.

BACKGROUND OF THE INVENTION

The present invention relates to an automated procedure for optical analysis of structures, in particular, for analysis and determination of biological, cellular structures, as well as an apparatus for this purpose.

To help with disease recognition, microscopic changes of components and structures can be used along with chemical and biological analysis of samples from biological organisms to determine presence of diseases and monitor their progression. To simplify these types of biological and chemical determinations, increased automation is being used. This reduces cost and increases speed. Microscopic observations, however, are still performed by an experienced person.

Apparatuses for automated and semi-automated analyses of chemical and biological substances and parameters are generally known. For example, WO 2006/00015 describes an apparatus and a process for arranging pipettes and dispenser tips in a system for manipulating liquid samples. Such an apparatus includes a robotic manipulator for aligning pipettes and dispenser tips in direction X and at a right angle to this in direction Y in or on sample holders arranged within the system. Such apparatus typically also include the ability to move pipettes and dispenser tips vertically up and down, in the direction Z, with respect to the directions X and Y. It is advantageous if the sample holders can be directed along the workbench. Liquid samples can be present in the wells of microtiter plates or can be pipetted into these from sample tubes. Typically, two microtiter plates are arranged on a so-called plate carrier, which preferably can also be directed along the workbench. This sort of analysis device is distributed by Aesku.Systems GmbH & Co. KG, Wendelsheim, DE under the name Helmed.

CH 696 030 A5 describes an apparatus for manipulation of samples in holders and/or on a slide within a described field X-Y, in which the first and second robotic manipulators are able to be used on at least the entire area of the X-Y field, without interfering with one another. The field of action for both robotic manipulators can be freely selected. The second robotic manipulator is able to pass by the first robotic manipulator both, when loaded or unloaded with objects. The relocation of diverse objects by the second robotic manipulator, such as transfer of active devices such as scanners (1 D, 2D), cameras, printheads, etc., enables use of these devices across the entire field of the working platform.

A storage unit for biological samples consisting essentially of a main horizontal surface with multiple storage chambers is described in EP 1 829 613 A1. Biological samples, such as tissue samples obtained by biopsy, are often stored as tissue pieces in cassettes or thin sections on slides for use in biological laboratories, and in particular in pathology laboratories within universities and hospitals. A selection of such cassettes and glass slides is provided, for example, by Thermo Shandon.

In WO 2005/103725 A1, an apparatus for transporting or studying fluids in a system for working with liquid samples is described. The apparatus includes at least one functional element with at least one functional end, whereby the functional element is generally perpendicular (vertical) to the working field in a Z-direction.

DE 10 2007 018 483 A1 describes a working platform for handling of liquids, such as pipetting of liquids from receptacles and their distribution in wells of a microtiter plate, generally known through the documents WO 02/059626 A1 (entitled "Pipetting Device") and EP1 477 815 A1 (entitled "Device for precisely approaching microplate wells"). In particular, the invention describes working platforms in which for example, pipette tips are brought automatically to a particular location.

In WO 2007/071613 A1, an apparatus for conditioning system fluids for a liquid handling device is described, wherein the following state of the art is referred to. Branches of industry, such as pharmaceutical research and in clinical diagnostics, which involve biochemical techniques, require installations for processing of liquid volumes and fluid samples. Automated installations typically include a liquid handling device, such as a single pipetting device or multiple pipetting devices that can be used with fluid reservoirs located on the workbench of a workstation, or form part of a liquid handling workstation.

EP 1 206 967 A2, describes that a droplet with a volume of greater than 10 µl can simply be released into the air because, with correct use of the pipette the droplet exits the pipette tip of its own accord. The droplet size is dependent on the physical characteristics of the sample fluid, such as surface tension and viscosity. Thus the drop size limits dispersion of the quantity of liquid to be dispensed. EP 0 725 267 A2 describes a pipette tip in the form of a microinjection pump with which a fluid sample can be actively separated. Subsequently delivery of fluid occurs via the hydrostatic pressure in the tubing between storage reservoir and pipette tip.

Under the presently known systems such as those known for example in WO 2006/000115 A1. WO 02/059626 A1 and EP 1 477 815 A1, it is common that all eight wells or positions of a microtiter plate are simultaneously filled and washed, and reagents added using eight equidistant hollow needles (cannula).

EP 1 921 552 describes a network controlled procedure for ensuring authenticity and quality of visually obtained laboratory diagnostic findings based on manual or semi-automated medical laboratory analyses using indirect immunofluorescence. By electronically networking the sample processing steps the laboratory system used for this minimizes human sources of error, while at the same time guaranteeing that visually obtained findings depend on a correct and error free patient sample associated data base. Nevertheless, the visually obtained findings depend on an assessment of the fluorescence patterns obtained and are therefore based on a manual step.

It is often necessary to optically study biological and chemical reactions of biological systems using for example tissue fragments, whole cells or even cell components such as cell organelles. This is achieved by viewing and analyzing the objects of study under a microscope, whereby to date this typically involves visual assessment and sorting based on the subjective experience of the user.

SUMMARY OF THE INVENTION

The present invention aims to avoid the above mentioned disadvantages associated with state of the art, refrain from using manual steps in optical assessment and achieve a high level of system stability.

The objective of the invention is to provide, particularly for material from biological samples, a procedure and apparatus for recognition and optical analysis of two and/or three dimensional structures that uses microscopic analysis without the need for human intervention. Based on these structures, the invention also aims to recognize typical conditions associated with disease or anomalies. Another objective of the invention is to perform this optical analysis in an apparatus together with a chemical and biological analysis.

According the present invention, the objectives are realized through the defined characteristics. Further advantageous developments of the invention are also provided.

In accordance with the invention, the procedure involves use of an automated optical device to microscopically analyze samples from, for example, biological material such as cells, tissue and/or cell components. It involves capture of an image of the sample via an optoelectronic system and its storage on an electronic storage device. The so captured and stored image is then compared with a collection of images and partial structures stored in a database. Such a comparison can be performed for example, by using an algorithm to carry out the so called "best fit" method. Thus, possible characteristics or structures can be recognized within the image and categorized according to their pattern. In this way it is possible to routinely categorize both natural and unnatural, and in particular malignant, changes without the influence of human intervention.

To enable such computer-assisted recognition of the two and three dimensional structures, the image must be very precisely captured, whereby the optical device must have the sample of study exactly in focus. According to the invention, this is possible through a combination of contrast analysis and recognition of the color values.

In accordance with the present invention, this is achieved by altering the distance between the optical device and the sample present in the sample holder until the sample is in focus.

The invention states that this is achieved using a computer-driven sliding device that controls the distance between the sample and the optical device by analyzing contrast and comparing color values.

Using both processes, a point is reached at which contrast and color value both reach their maximum and a stop signal is generated. This stops further changes in distance from optical device to sample. In this way, an autofocusing system can be maintained that avoids the need for human intervention and at the same time enhances system stability. It is noteworthy that the use of additionally labeled positive/negative cells as controls can be avoided. Similarly, according to the invention, the procedure also avoids the need for special exposure settings and provides a safeguard against misfocusing, in particular dust focusing.

Typical procedures for contrast analysis are generally well known and commercially available. In accordance with the invention, the analysis of color value is performed such that a pattern of different colors is mapped and the position of the optical focus and/or the position of the sample are continuously changed until a maximum number of different, separate color pixels is reached. The preferred colors used are, according to the invention, red, green and/or blue. Algorithms for analysis of color values are generally well known and are available on the internet and commercially, for example from Keyence.

In a preferred embodiment of the invention, the sample receptacle has contrast characteristics such as lines, dots, diamonds etc. which may also be colored. These characteristics are preferably so arranged that they are not on the receptacle, but are placed as near as possible to it. Using such characteristics together with the above described autofocusing, it is possible to recognize any tilting of sample receptacles and adjust for this. This is particularly advantageous when multiple sample receptacles are arranged adjacent to each other such that they form a multiwell plate.

Typically, due to the limited depth of focus of most optics, it is not possible to generate sharply focused images of spatially large samples such as cells.

Using the autofocus procedure described in the invention, it is now possible by adjusting the height, to focus on a spatially large sample for example, at different depths. After storage of the generated images it is possible to overlay these to form a two or three dimensional structure of the sample. This is achieved by generating multiple images at each focal depth and "stitching" these together to create a single image. These so-called stitching procedures are generally well known and can for example, be downloaded free from the internet. Using the stitching procedure it is also possible to generate sharply focused images by combining images that are only partly in focus (and therefore only partly visible) with other images, to provide an entirely in focus image that could not be visualized manually.

In another embodiment of the invention the sample, typically present in fluid, is so prepared that the sample surface is as level as possible. This is achieved for example, by addition of only minimal quantities of fluid, or by removal of fluid after application.

It has proven useful after removal of fluid to protect the sample from drying out by for example, covering with a coverslip, or by inhibiting any increase in the liquid vapor pressure above the sample.

The analysis apparatus can for example, be like that described in DE 10 2008 022 835 with the addition of an electro-optical device.

In the context of the present invention, a microscope can be a movable microscope such as a typical light microscope, a laser microscope and in particular, a scanning microscope, in particular a laser scanning microscope.

A sample is a biochemical or chemical sample. Above all, the sample can be present in a test tube, a small pot or well, or on a sample carrier, especially a microscope slide. The sample itself may consist of cells, both live or dead, viruses, RNA- and DNA-molecules, or cell components such as organelles or membranes.

Electronic detection and image generation of the sample using an electro-optical device occurs preferentially by placing the sample directly under the rays of the microscope or optic. The generated images are sent to a transducer, where they are converted from light signals into electronic signals. This preferentially uses a CCD device.

Electronic, mechanical autofocusing is achieved using a sliding device that is computer-driven by contrast analysis and color value detection. Contrast analysis using known algorithms is used to relocate the optics and/or the sample in a vertical direction (z-axis) thus optimizing contrast. This allows the sample to come to rest within the optical focus of the microscope. Color value detection involves for example, separate determination of pixel numbers for different colors, such as red, green or blue, within the electro-optical device, so as to generate a separate pixel maximum for each color. Furthermore, it is possible for example to locate adjacent to the sample, a focusing layer that contains markers such as lines, dots or diamonds in different colors, so that focus presetting can take place and, in particular, rapid automatic detection of the correct focal setting can occur.

Additionally, it is possible to include a focusing layer for each individual sample. This means in other words that when multiple samples are present, as for example in a multiwell plate, the focusing layer may be present at different locations on the surface or side of the plate. This is advantageous in that detection of differences in height, as for example when the sample is tilted, can be more quickly determined over the entire multiwell plate A further embodiment of the invention comprises procedures that additionally involve processing of the sample. This may, for example, involve bringing a sample to be studied on a slide in a test tube into contact with other biochemical or chemical compounds, in particular in solution, so that biochemical or chemical reactions can occur. A waiting time, such as an incubation period, and/or a mixing period, may also be involved in this process, in which case the sample will not be assessed by the electronic device until after the waiting period is complete.

Another embodiment of the invention relates to the covering of the sample with a covering fixture. This may take the form of a glass plate, a plastic plate or other light permeable plate. Likewise the samples may be covered by addition of a drop of fluid, for example when they are present on a slide. Care should be taken that this does not lead to an impairment of the microscopic image. This can be achieved by use of coated slides to reduce surface tension, by addition of surface tension reducing agents, or by simply adding a small volume of fluid.

Another embodiment of the invention comprises a procedure involving computer-based differentiation of structures, such as histograms, using a database/library. This involves implementation of positive or negative recognition to the effect that through use of a mathematical classification based on an algorithm, image information is shown such that it depicts positive or negative structures, in particular characteristic grids, structures or patterns.

A further embodiment of the invention is an analytical device for performance of the procedure associated with the invention.

BRIEF DESCRIPTION OF THE FIGURES

Other advantages and advantageous embodiments of the invention are exemplified in the drawings and the following description. It should be noted that the drawings are of descriptive quality only, and do not restrict the invention in any way.

DETAILED DESCRIPTION OF THE INVENTION

Figure 1:
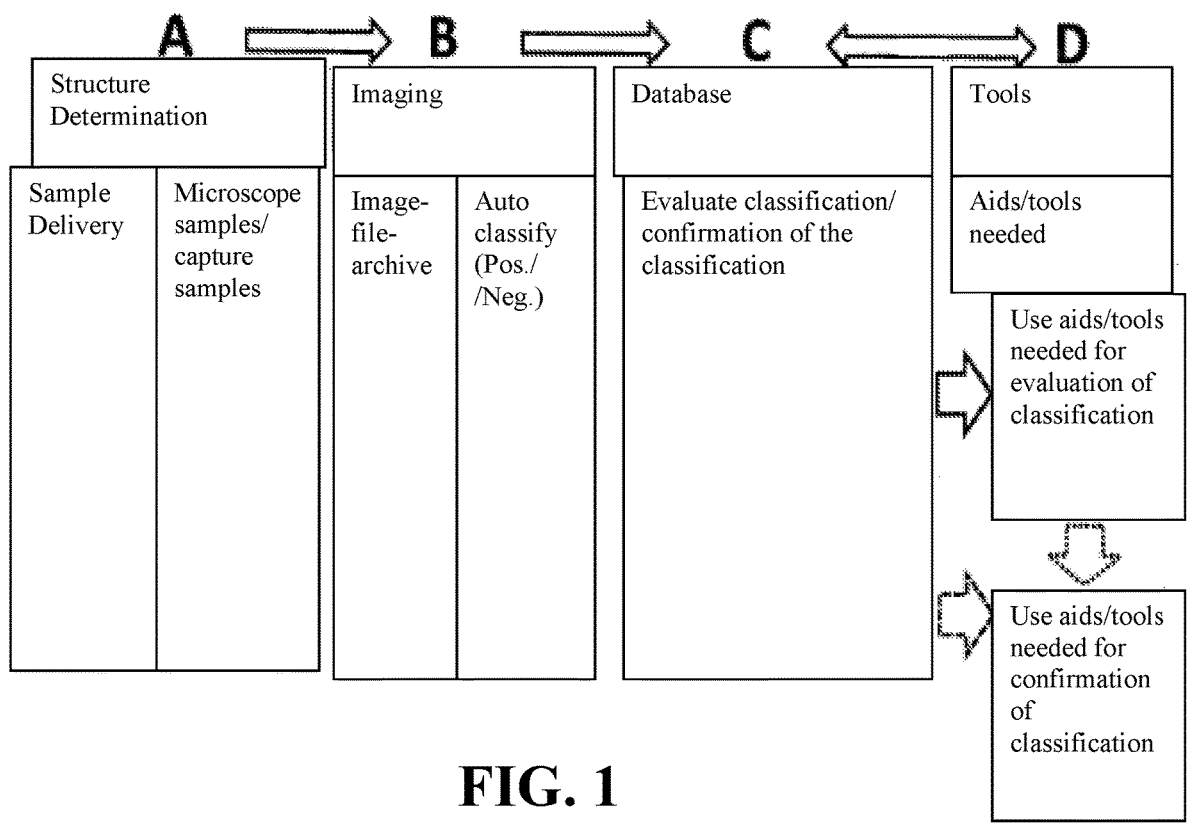
FIG. 1 shows an example of a procedural model in the form of a flow diagram.

FIG. 1 shows an example of a model based on the procedures embodied in the present invention. The step shown in Block A (Structure Determination) consists of sample provision comprising sample identification via a barcode reader integrated into the analytical device, loading of the device with the reagents for the required test and subsequent start of the fully automated immunofluorescence test sample processing and automated microscopy and/or detection of samples. Autofocusing is achieved with the help of contrast analysis and color value detection prior to the generation of electronic images using a CCD-camera. In Block B (Image Processing), the images generated are processed using a data processing software and stored in an image- and data-archive for later use in an automated classification (pos/neg) procedure using histograms. The step in Block C (Database) serves to ensure diagnosis and confirm classification, whereby the tools depicted in Block D (Aids/Tools) can be used. To complete the process a suggested diagnosis is generated.

Figure 2:
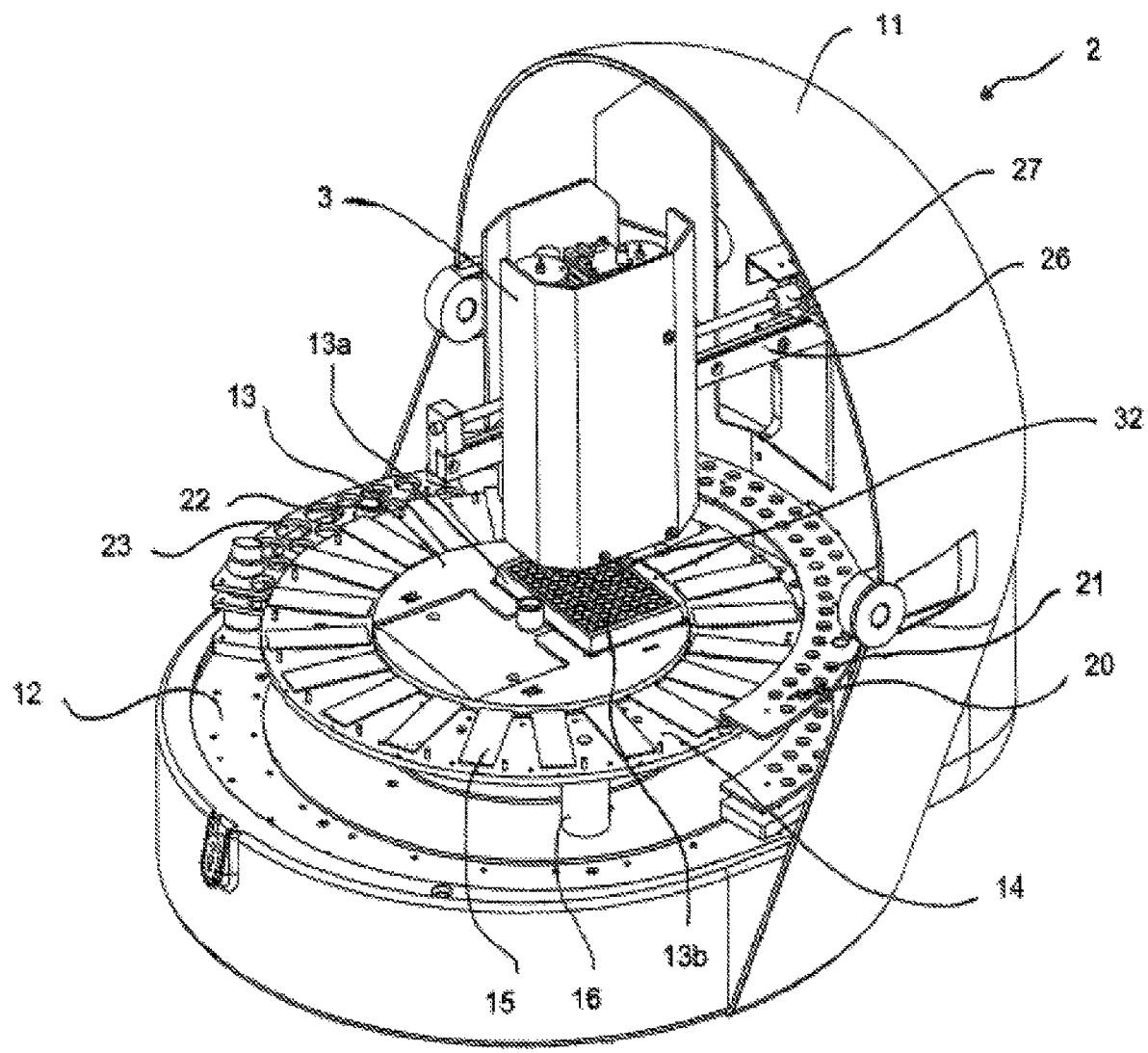
FIG. 2 shows a schematic representation of the analytical device as described in the invention, but without microscope.

FIG. 2 shows a perspective view of the analytical device 2 as described in the invention for the study of biological and chemical samples 5 that is used as an analytical apparatus 2. The analytical apparatus 2 has a helmet shaped device housing 2 with a raised visor-like lid 3, that can be raised and lowered (open and shut) via two hinged joints 4. Electrical sockets are located on the rear (not shown) and include diverse sockets for the 24 V electrical network, for electrical control signals to a data processing system (personal computer) and for test signals (in particular USB sockets).

The analytical apparatus 2 has a baseplate 12 on which a worktable 13—often referred to as carousel—is mounted. This is horizontal when in use and can be turned around its vertical axis at predetermined angle φ. Two rectangular recesses are envisaged in the inner worktable 13 for placement of two sample holders 13 a, whereby only one sample holder with multiple recesses or wells 13 b in a matrix arrangement is shown. This inner worktable 13 is enlarged radially with a ring-formed worktable 14 on which transparent slides carrying biological or chemical samples are mounted in direction of the circumference. The ring-formed worktable 14 is fastened to the baseplate 12 by supports 16. The ring-formed worktable 14 can be turned separately from or together with the inner worktable by mechanisms not shown that involve a separate rotary drive. A semicircular test tube rack 20, containing holes 21 for small test tubes, is envisaged radially outside the ring-formed worktable 14. Also envisaged is a tube rack with larger holes 23 for larger tubes 24, this is a quarter of a ring in the same circumferential area as, shown in the left side of FIG. 2.

A sample manipulator 3 is located above the inner worktable 13 attached to a horizontal support arm 26 parallel to the inner worktable with a horizontal direction extending movable screw-driven 27 carriage (not visible). This carriage moves the needle system containing the needle unit 32 in a vertical Z-direction. In this manner, it is possible to position the needle unit 32 in a position above and a position in the well 13 b of the sample holder 13 a.

Figure 3:
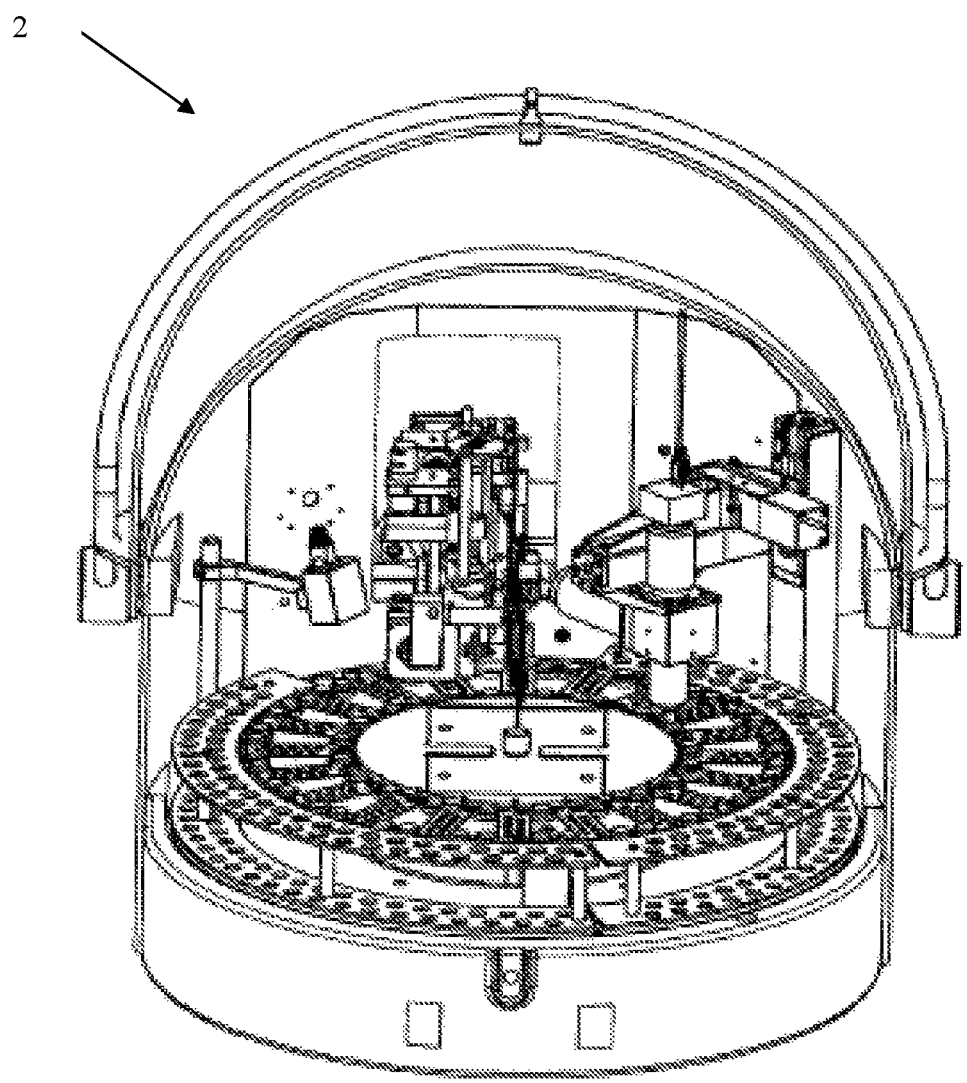
FIG. 3 shows a schematic representation of the analytical device as described in the invention including microscope.

FIG. 3 illustrates the location of the microscope and is based loosely on FIG. 2.

What is claimed:

1. An analytical apparatus for automated optical analysis of chemical and/or biological samples comprising,
   (a) a sample holder introducing the sample to be studied;
   (b) a sensing unit present;
   (c) an electro-optical unit used to generate an electronic image of the two and three dimensional structures present in a sample;
   (d) a data storage medium for storage of the image;
   (e) a computer controlled sliding device for enabling optical focusing of the image;

(f) an electronic database containing stored two and three dimensional structures;

(g) a processing unit for comparison and categorization of electro-optically generated images of two and/or three dimensional structures using structures present in the database; and (h) an output unit for the structures categorized in the comparison, wherein the computer controlled sliding device uses contrast analysis and color value detection to control the distance between the sample and the electro-optical unit;

(i) a device casing with a baseplate;

(j) a microscope;

(k) a worktable for accepting samples that is horizontally aligned with the baseplate;

(l) a sample manipulator located above the worktable attached to a horizontally extending support arm with a horizontally screw-driven carriage; and (m) a movable hollow-needle system attached to the carriage that moves in a vertical Z-direction and consists of three hollow-needles separated by a distance selected as small enough to enable all three needles with their hollow-needle tips to be positioned and inserted in the same receptacle or well at the same time.

2. The apparatus according to claim 1, wherein the optical unit has a microscope that communicates with an electronic camera.

3. The apparatus according to claim 1, wherein the sample holder has at least one marking that can be used for contrast analysis and color value detection.

4. The apparatus according to claim 1, wherein the sample holder has at least one marking that can be used for contrast analysis and color value detection.

5. A procedure for automated optical analysis of two and/or three dimensional structures of chemical and/or biological samples in a sample holder, comprising:

generating an electronic image of two and/or three dimensional structures present in the sample by an electro-optical unit of an analytical apparatus for automated optical analysis of chemical and/or biological samples, the analytical apparatus also comprising:
a sample holder introducing the sample to be studied,
a sensing unit,
a data storage medium for storage of the image,
a computer controlled sliding device for enabling optical focusing,
an electronic database containing stored two and three dimensional structures,
a processing unit for comparison and categorization of electro-optically generated images of two and/or three dimensional structures using structures present in the database,
an output unit for the structures categorized in the comparison, wherein the computer controlled sliding device is configured to use contrast analysis and color value detection to control the distance between the sample and the electro-optical unit,
a device casing with a baseplate,
a microscope,
a worktable for accepting samples that is horizontally aligned with the baseplate,
a sample manipulator located above the worktable attached to a horizontally extending support arm with a horizontally screw-driven carriage, and
a movable hollow-needle system attached to the carriage that moves in a vertical Z-direction and has three hollow-needles separated by a distance selected as small enough to enable all three needles with their hollow-needle tips to be positioned and inserted in the same receptacle or well at the same time;

storing the generated electronic image in the data storage medium;

optimally focusing by altering the distance between the sample and the electro-optical unit using the computer driven sliding device, the sliding device being controlled based on the contrast analysis and the color value detection;

comparing two and/or three dimensional structures of the generated image with known structures present in the database; and capturing images of the two and/or three dimensional structures of the generated image that the electro-optical unit categorizes using algorithms according to characteristic grids, structures or patterns.

6. The procedure according to claim 5, wherein the color value detection occurs when the number of different color pixels reaches a maximum number.

7. The procedure according to claim 6, wherein the sample holder includes a receptacle and/or a plate with multiple sample receptacles that are coded so that structures can be categorized.

8. The procedure according to claim 5, additionally comprising: including covering of the sample with a covering fixture.

9. The procedure according to claim 8, wherein the sample holder includes a receptacle and/or a plate with multiple sample receptacles that are coded so that structures can be categorized.

10. The procedure according to claim 5, additionally comprising: including covering of the sample with a covering fixture.

11. The procedure according to claim 10, wherein the sample holder includes a receptacle and/or a plate with multiple sample receptacles that are coded so that structures can be categorized.

12. The procedure according to claim 5, wherein the sample holder includes a receptacle and/or a plate with multiple sample receptacles that are coded so that structures can be categorized.

* * * * *